United States Patent
Zhong et al.

(10) Patent No.: US 11,970,621 B2
(45) Date of Patent: Apr. 30, 2024

(54) AMYLOID-BASED FUNDAMENTAL BUILDING MATERIAL WITH INTEGRATED GENETICALLY PROGRAMMABLE FUNCTIONALITY

(71) Applicant: ShanghaiTech University, Shanghai (CN)

(72) Inventors: Chao Zhong, Shanghai (CN); Yingfeng Li, Shanghai (CN); Ke Li, Shanghai (CN)

(73) Assignee: ShanghaiTech University, Shanghai (CN)

( * ) Notice: Subject to any disclaimer, the term of this patent is extended or adjusted under 35 U.S.C. 154(b) by 816 days.

(21) Appl. No.: 17/092,261

(22) Filed: Nov. 7, 2020

(65) Prior Publication Data
US 2021/0071016 A1 Mar. 11, 2021

Related U.S. Application Data

(63) Continuation of application No. PCT/US2019/031397, filed on May 8, 2019.

(30) Foreign Application Priority Data

May 8, 2018 (WO) ................ PCT/CN2018/085988

(51) Int. Cl.
*C09D 11/04* (2006.01)
*B29C 39/00* (2006.01)
*B29C 39/22* (2006.01)
*C07K 14/00* (2006.01)
*C07K 14/245* (2006.01)

(52) U.S. Cl.
CPC ............ *C09D 11/04* (2013.01); *B29C 39/006* (2013.01); *B29C 39/22* (2013.01); *C07K 14/001* (2013.01); *C07K 14/245* (2013.01); *B29K 2089/00* (2013.01)

(58) Field of Classification Search
CPC ....... C09D 11/04; B29C 39/006; B29C 39/22; C07K 14/001; C07K 14/245; C07K 2319/21; C07K 2319/01; C07K 14/4711; C07K 2319/30; B29K 2089/00; B82Y 30/00

See application file for complete search history.

(56) References Cited

U.S. PATENT DOCUMENTS

2019/0315799 A1* 10/2019 Joshi ................ C07K 14/47
2021/0230244 A1* 7/2021 Gupta ................ A61K 38/00

* cited by examiner

*Primary Examiner* — S. Behrooz Ghorishi
(74) *Attorney, Agent, or Firm* — Richard Aron Osman

(57) ABSTRACT

A material fabrication method comprises (a) fabricating a structure from a programmable amyloid material (PAM) ink comprising an amyloid monomer stabilized in a liquid solvent; and (b) contacting the structure with an agent which triggers polymerization of the amyloid monomer and stabilization of the structure.

22 Claims, No Drawings

AMYLOID-BASED FUNDAMENTAL BUILDING MATERIAL WITH INTEGRATED GENETICALLY PROGRAMMABLE FUNCTIONALITY

INTRODUCTION

Researchers in a variety of industries continually seek new soft materials, including bio-inspired materials, that offer functional flexibility and that can be crafted into useful structures using standard fabrication techniques. Some popular bio-inspired and biological materials that have received considerable research attention in materials science include, among others, peptides, lipids, DNA, silk, and phage coat proteins, each with their own attributes and limitations. For example, peptides, lipids, and DNA can be used for programmable assembly, but are not suitable for genetic engineering of protein-domain based functionalities. Alternatively, silk, and phage coat proteins are suitable for use with diverse fabrication techniques like lithography, printing and spinning, and are in principle amenable to genetically engineerable functionalities. However, applications have been limited, and structures built from these materials do not typically offer strong long-term stability, particularly in harsh conditions.

Natural biofilms can be highly resistant to harsh environmental conditions, and bacterial biofilms provide rich resource for bio-material prospecting. One of the key functional attributes of the components that comprise these films is their intrinsic ability to self-assemble into complex and ordered hierarchical structures across multiple spatial scales. For example, Curli are a class of highly aggregated secreted extracellular bacterial amyloid fibers built from self-assembled CsgA protein monomers, and are involved in the colonization of surfaces and in biofilm formation. Curli are rich in β-sheets, are remarkably strong, and assist bacteria to adhere to a variety of surfaces and to resist environmental insults. Theoretical vantages of functional amyloid materials over phage-coat-functional materials stem largely from the particular chemical composition of the amino acids that form their β-sheets. Specifically, the monomeric protein that ultimately form amyloid polymers are strongly enriched for serine, alanine, glycine, asparagine and glutamate, amino acids that readily form complex networks of hydrogen bonds; these hydrogen networks are known to be a primary source of the high resistance of amyloid biofilms to harsh conditions. We here exploited the self-assembly ability of the amyloid monomers to generate a new class of functional bio-materials that we refer to as programmable amyloid materials (PAMs).

SUMMARY OF THE INVENTION

The invention provides compositions comprising programmable amyloid materials (PAMs), and related methods of fabrication and use.

In an aspect the invention provides a material fabrication method comprising: (a) fabricating a structure from a programmable amyloid material (PAM) ink comprising an amyloid monomer stabilized in a liquid solvent; and (b) contacting the structure with an agent which triggers polymerization of the amyloid monomer and stabilization (curing) of the structure.

In embodiments:
the fabricating step comprises micro-transfer molding, embossing, spin-coating, dip-coating, electro-spinning, spraying, brush, lithography, electro-spinning, etc.
the amyloid monomer is CsgA, FUS, TDP, TasA etc.
the monomer is functionalized with one or more functional groups, such as in the C and/or N terminus (e.g. of CsgA), groups including active enzymes, isopeptide tag systems like SpyTag, cell affinity tag like RGD, or other functional peptides like antibacterial, cell proliferation or differentiation, templated growth of inorganic nanoparticle,
the solvent is a polar solvent like HFIP, TFA, etc. which serves as a strong hydrogen-bond-donor, and which solubilizes the amyloid through hydrogen bond disruption, but acts as a poor hydrogen bond-acceptor, and which does not form bonds with the amyloid monomer, wherein the solvent can dissolve amyloid structure and disrupt β sheets structures over time.
the curing agent is an alcohol like methanol, ethanol, isopropanol and PEG, $H_2O$ (including buffer KPI, PBS, Tris), which can trigger intrinsic amyloid assembly but maintain the original morphology of created structures.
the contacting (curing) step comprises a two-step cure: first contacting with a first cure agent in vapor phase, and second contacting with a second cure agent in liquid phase, wherein the first and second cure agents are preferably the same. For PAM coatings with non-patterned structures, a one-step cur in solution will often suffice; however, a two-step (vapor followed solution) cure is preferred, especially for PAM patterned structures. To cure patterned structures with other agents (such as $ddH_2O$, KPI buffer or isopropanol), a two-step curing process is also preferred; however, compared with curing with methanol vapor coupled with methanol immersion, the curing generally takes longer time because $H_2O$ and isopropanol are less volatile compared to methanol.
the structure is selected from: 2D and 3D arrays and self-supporting patterned porous PAM sheets (PPPS) etc., including diverse surfaces and interfaces (2D hydrophobic or hydrophilic surfaces, 3D irregular interfaces, microfluidic devices, medical implant surfaces etc.), uniform coatings or patterned structures, magnetic sheets, cell sheets, etc., and the sheets are useful in a wide variety of applications, such as quantum dot binding and protein conjugation and mineralization.
after the contacting step the structure regains β-sheets after curing, and remains ultra-stable, e.g. structurally and/or functionally stable after challenge with a wide range of harsh conditions (high temperature, e.g. 90 degree) and low temperature (e.g. −80 degree), organic solvents, solutions of a wide range of pH=2-12), and have long-term stability at ambient conditions.
the method further comprises selectively degrading the structures with an enzyme such as trypsin or protease K for CsgA and $csgA_{CBD}$, or chitinase for chitin.

In aspects the invention provides programmable amyloid materials (PAMs) produced by the subject fabrication methods and methods of using the materials and fabricated material structures.

The invention includes all combinations of recited particular embodiments as if each combination had been laboriously recited.

DESCRIPTION OF PARTICULAR EMBODIMENTS OF THE INVENTION

The embodiments and examples herein are provided by way of illustration only and not by way of limitation. Those skilled in the art will readily recognize a variety of noncritical parameters that could be changed or modified to yield essentially similar results.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Modular genetic design for molecular PAMs. We used two distinct harvesting methods to obtain CsgA and functionalized ($R_1$-CsgA-$R_2$) nanofibers: direct harvest of secreted nanofibers from cultured biofilms or traditional recombinant protein expression and purification methods. We found that CsgA backbone can still self-assemble into nanofiber after domain incorporation PAMs ink for biofabrication (structural restoration confirmation). The CsgA proteins that form amyloid nanofibers begin to self-assemble into nanofiber structures immediately after purification in aqueous solution. However, our new amyloid materials required that we find a way to prevent the self-assembly nanofibers until the CsgA monomers were in situ in their desired location. An insight that unlocked this problem is that a solvent like hexafluoroisopropanol (HFIP) can disrupt the secondary structure of aggregated CsgA (including hydrogen bonds). Thus, harvested aggregated CsgA nanofibers can be dissolved in HFIP to make an "ink" of soluble CsgA monomers. Before attempting any fabrication using CsgA, we characterized the morphology and structure of this material before and after exposure to methanol. Results from AFM height imaging, circular dichroism analysis, and ATR-FTIR all showed that HIFP exposure did not alter the ability of CsgA monomers to self-assemble into their typical nanofiber structures. We next confirmed that exposure to methanol does trigger renaturing of the CsgA monomers into CsgA-PAM nanofibers. The Young's modulus of both denatured and renatured PAM was measured by peak force quantitative nanomechanical (PFQNM) AFM and nanoindentation; the renatured PAM was almost twice as denatured. Owing to the hierarchical structures of the CsgA nanofibers, renatured PAM had Young's modulus comparable to that of natural dragline silk (0.1~12 GPa).

PAMs integrated with diverse biofabrication tools. The HFIP ink is a truly flexible substance that can conceivably be used in any fabrication method amenable to organic solvents (micro-transfer molding, embossing, spin-coating, dip-coating, electro-spinning, spray, brush, lithography, electro-spinning, etc.).

Patterned PAMs structures through microtransfer molding and structural stability confirmation with various conditions. As our design emphasized patterned fabrication, we initially concentrated on a micro-transfer molding process using CsgA/HFIP ink in combination with polydimethylsiloxane (PDMS) stamping that allowed for highly precise deposition of CgsA in its monomer form. Following their deposition (here in hierarchically defined micro- and even nano-scale patterns), the CsgA monomers are exposed to methanol vapor or solution which again triggers their self-assembly in situ ("curing process") We first printed CsgA-PAM into large scale (~1 cm²) patterned arrays with a spider web motif. After exposure to methanol, the printed CsgA-PAM was ~1 µm in width with obvious nanofiber bundles that hierarchically assembled into larger microthreads. No nanofibers features were observed for control printed CsgA that was not exposed to methanol. X-ray fiber diffraction, Raman spectroscopy, and AFM-IR analyses all revealed that whereas control printed CsgA was amorphous, printed CsgA-PAM occurs as R-sheet structures.

Both the structural stability of a given biomacromolecular building material and its motif fidelity are well known performance attributes that will affect its suitability for use in making patterned structures, so we carefully characterized the stability and morphology of PAM after exposure to a large variety of harsh conditions. We printed and cured linear "test threads" of CsgA-PAM on silica substrate and exposed them to high temperature (90° C.), low temperature (−80° C.), aqueous solutions (pH=2, 12), and common organic solvents (hexane, acetone, chloroform, isopropanol, and DMF) as representative extreme conditions. We also exposed test threads to ambient conditions for 6 months to examine longer-term stability.

Firstly, ATR-FTIR analysis comparing unchallenged renatured CsgA-PAM with challenged revealed only negligible changes to the molecular structure with each of the challenge conditions. We next characterized the motif fidelity of the CsgA-PAM test threads after challenge. AFM images showed that the test threads retained their original parallel pattern morphology, and from quantitative comparison of the heights of the test threads showed only negligible changes after high temperature (90° C.), low temperature (−80° C.), aqueous solution (pH=2, 12), hexane, acetone, and isopropanol; chloroform and DMF challenge reduced the heights of the test threads by, respectively, 19.7 and 34.6% compared to unchallenged control threads. These results demonstrate the ultra-stability and motif fidelity of CsgA-PAM and performance advantages over many currently available biomacromolecular building blocks like silk, phage, peptides and lipids, that are prone to denature or dissolve in slightly sub-optimal conditions, making their patterns disappear in a very short time.

Patterned PAMs for potential applications. Demonstrating the utility of the ultra-stable PAM materials, we also used PDMS stamps that have been used to make nanodevices that function as diffractive optical elements (DOEs). Other optically-diffractive materials often used to make DOEs (e.g., polymethylmethacrylate and polycarbonate) are unstable in organic solvents. We printed CsgA-PAM into patterns on glass substrates (2D and 3D) and treated them with harsh conditions including acetone or pH 2 challenges for 24 h. Upon illumination, these CsgA-PAM nanodevices emitted their particular transmission diffraction patterns, including for example a dot array and an inverted Chinese character "fú". Later, we illuminated multi-layered combinations of these and generated an inverted character overlapping projection. These DOEs highlight how the high spatial resolution fabrication and ultra-stability in harsh conditions of the PAM material represent highly attractive performance characteristics for difficult applications.

To functionalize PAMs we used genetically engineered CsgA monomers that had a polyhistidine-tag fused to their C-terminal ends (CsgA$_{His}$). We used microtransfer molding of PAM ink to make arrays of triangle patterns on glass slides and cured the CsgA$_{His}$-PAM with methanol vapor. The histidines on the patterned CsgA$_{His}$-PAM were then reacted covalently with quantum dots (QDs) encapsulated in nitrilotriacetic acid (NTA) and bound to Ni$2^+$ to form arrays that could emit green fluorescence upon excitation at 488 nm. We also used inverted PMDS stamps to fabricate micropatterned porous films that we reacted with a 1/1 mixture of green and red emitting QDs and tested their respective and collective emission properties. We next built a prototype field effect transistor (FET) based on the patterning of $CsgA_{His}$-PAM into parallel lines patterns and reacting them with of red-emitting QDs. Their typical output and fitting transfer performance were derived. We also reacted gold nanoparticles capped with Ni-NTA with our patterned $CsgA_{His}$-PAM to generate functional organic/inorganic hybrid patterned structures that have many potential applications in bionanoelectronics.

Moving beyond the initial $CsgA_{His}$-PAM applications with inorganic functional components, we next generated CsgA monomers with C-terminally fused SpyTagor SnoopTag peptides ("$CsgA_{SpyTag}$," "$CsgA_{SnoopTag}$," two tags that can undertake spontaneous isopeptide bond formation with their respective SpyCatcher and SnoopCatcher binding partners). We used PMDS stamps to fabricate micropatterns from $CsgA_{SpyTag}$-PAM and $CsgA_{SnoopTag}$-PAM and then reacted these with mCherry-SpyCatcherfusion proteins and GFP-SnoopCatcher fusion proteins. Testing these materials with appropriate excitation energies successfully demonstrated that CsgA monomers bearing peptide components can survive the PAM ink preparation, printing, and curing steps of the PAM fabrication process with their functionality intact. These results indicate that PAMs can, either directly or through technologies like isopeptide bond peptide partnering, be used in applications requiring precise reactivity of biomolecules.

To get large-scale patterning, we adopted commercial water-proof stickers with motifs as mask. Substrate bound with stickers were covered by fresh made CsgA monomers. The following day, after NPs or QDs binding, the patterning only existed on the part which was not covered with stickers after peeling the stickers. Polytetrafluoroethylene (PTFE) owned a hard-modified surface. The contact angle of PTFE was decreased from 110° to 77°, from hydrophobic to hydrophilic after CsgA coated. Under 254 nm ultraviolet irradiation, quantum dots were excited and emerged designed patterning. Additionally we coated CsgA on polypropylene (PP) pipes and non-woven fabrics. After Au NPs binding and gold enhancement, the fabrics formed conductive mesh. Polydimethylsiloxane (PDMS) and polyethylene terephthalate (PET) were commercial substrate in electronics. CsgA formed coatings as well and the gold enhancement made the patterning work as conductor in electronic circuit. The CsgA patterned PET substrate kept the intrinsic transparency and flexibility while endowed with underwater QDs affinity.

To get 3D patterning as CsgA was as interface nanomaterial we took an alternative approach that used CsgA as 3D coatings. To achieve this embodiment, we adopted several demonstrations. PDMS micro-pillars with 100 μm diameter and 50 μm height were treated with oxygen plasma followed by CsgA monomer solution covered overnight. After washed and bound, 3D QDs PMDS arrays were achieved. The 3D morphology was imaged by Laser Scanning Confocal Microscopy. By similar methodology we got fluorescent 10 μm Polystyrene (PS) and $SiO_2$ micro-spheres with QDs conjugated $CsgA_{his-tag}$ patch. By changing the mixing ration of red and green QDs, from 100%:0, 75%:25%, 50%:50%, 25%:75%, 0:100%, different color emerged on the CsgA-Histag patched PTFE spheres excited under 254 nm UV lamp. Gold nanoparticles coatings formed on the glass ball and a half of 3D printed cubic mold. These objects showed good conductivity following gold enhance procedures.

Self-supporting patterned porous PAMs sheets (PPPS) and applications. Given the ability to fabricate functionalized PAMs, we next demonstrated how various functional PAMs can be arranged creatively in physical space. To date, the materials available for the construction of biomacromoleclar patterns have been largely substrate-dependent (e.g. silk based lithography and phage based supramolecular structure). In nature, however, such patterns often occur as large-area functional free-standing structures, as for example with bacterial microcompartments and diatom cell walls. When we initially tried to make free-standing PAM structures by for example using water-soluble polyvinyl alcohol (PVA) as a sacrificial layer under molded patterns, we found that CsgA-PAM exhibit no sufficient cohesion with the PVA to maintain self-supporting microstructures after repeated washing with water. Our solution to this issue was the rational design of a self-supporting matrix inspired by a fascinating natural structure from cephalopods: squid beak is a soft biomaterials (i.e., non-mineralized) with extremely attractive mechanical properties (hardness and stiffness) that result from a protein-polysaccharide molecular interface wherein proteins with so-called chitin binding domains (CBD) act as linkers between separate chitin nanofibrils.

We generated CsgA monomers with C-terminally fused CBDs ("$CsgA_{CBD}$") and used a solution containing PAM ink of these monomers and dissolved chitin fibers to print patterned porous PAM sheets (PPPS) that exhibited a hierarchical nanofiber structure. The addition of the CBDs to the CsgA monomers clearly worked to provide increased structural integrity and increased elasticity to the PPPS, as the Young's modulus of the $CsgA_{CBD}$-PAM/chitin PPPS was higher than that of CsgA-PAM/chitin PPPS. Considering these results at the molecular level, the hydrophobic and aromatic amino acids of the functional CBDs bind with the sugar rings of the chitin fibers via hydrophobic and stacking interactions. Further, Quartz Crystal Microbalance (QCM) and Thioflavin T assays showed that the chitin nanofibers absorbed more $CsgA_{CBD}$-PAM than CsgA-PAM.

We next made PPPSs out of $_{SpyTag}CsgA_{CBD}$ and $_{SnoopTag}CsgA_{CBD}$ dual fusion monomers that featured functionalization at both their N-terminal (SpyTag or SnoopTag) and C-terminal ends (CBD). Excitingly, after reacting these materials with mCherry-SpyCatcher or GFP-SnoopCatcher binding partners to generate isopeptide bonds, testing of these materials with appropriate excitation energies successfully demonstrated that CsgA monomers that feature di-functional fusion moiety can be used to make multi-functional genetically engineerable bio-materials. Recalling the impressively strong and intricate patterns of mineralized materials known to occur in diatom cell walls, we made PPPSs out of $_{R5peptide}CsgA_{CBD}$-PAM; the monomers comprising this material have two functional fusion moieties: C-terminal CBDs and N-terminal $SiO_2$ nucleation peptides from *Cylindrotheca fusiformis* (R5). We exposed these PPPSs to a mineralization precursor solution of tetramethoxysilane, and both SEM and STEM-EDS methods confirmed successful biomineralization.

The extracellular CsgA secreted by pathogenic bacteria such as *E. coli* and *Salmonellacan* bind to polymers present on host cells (fibronectin). We demonstrated the bio-compatibilty of PAM by growing human embryonic kidney cells (WT, HEK 293T) on self-supporting $CsgA_{CBD}$-PAM/chitin PPPSs. Both wild-type and transgenic HEK 293T cells adhered to the PPPSs and grew as well as cells grown in a vessel lacking a PPPS. Our functionalized materials and structures are applicable to a broad range of applications exploiting the porous nature of the PPPSs for efficient mass transfer among cells and solutions (e.g., cell migration and invasion assay) as well as for applications that require cellular growth in precisely defined physical spaces (e.g., cell/materials interface, etc.).

The material fabrication methods are readily applied to alternative amyloid proteins, alternative solvents, and alternative curing agents. For example, material fabrication with alternative amyloid proteins were demonstrated with FUS low-complexity (LC) domains, an RNA-binding protein with essential roles in RNA transcription, processing, and transport, and which is enriched in four amino acids (glycine, serine, glutamine, tyrosine) at the N-terminus region of 200 amino acids of FUS, so that this FUC LC forms reversible amyloid structures. We also demonstrated fabrication with genetically engineered low-complexity domains, mefp3-TDP, a functional fusion amyloid protein based on TDP. Both patterned structures derived from the two proteins can be produced using the same protocol disclosed herein for example, microtransfer molding using amyloid/HFIP as ink, followed by curing with methanol (methanol atmosphere+methanol solvent).

Additionally, we demonstrated alternative solvents to dissolve various amyloid structures, including trifluoroacetic acid, and using a similar curing protocol, amyloid belta structures can be restored either for non-patterned and patterned structures.

Additionally, we demonstrated alternative curing agents could be used to cure belta-sheet structures of amyloid monomers. Besides methanol, low molecular weight polyethylene glycol (PEG, 400), isopropanol, ddH$_2$O and KPI buffer (pH=7.0~8.0) can also serve as curing agents. AFM height images confirmed the nanofiber feature of CsgA patterns.

Methods

1. Detailed Procedures for Plasmid Construction

Target gene fragments were amplified by PCR with appropriate templates and then were cleaved by restriction enzymes Nde I and Xho I (Fermentas Fast Digest) for 1 h at 37° C. The prepared fragments and the cleaved plasmid pET-22b treated with the same method were mixed and incubated with appropriate amount of Gibson Assembly Master Mix (NEB) for 1 h at 50° C., then transformed into BL21 (DE3) E. coli competent cells (TransGen Biotech). The strains were then smeared to the surface of LB media plates containing antibiotics to select the target strains. All constructs were sequence verified by Genewiz.

2. Detailed Procedures for Protein Expression, Purification

CsgA, CsgA-Spytag, CsgA-snooptag, CsgA-CBD, Spytag-CsgA-CBD, Snooptag-CsgA-CBD, R5-CsgA-CBD 20 mL LB containing CsgA plate was cultured overnight. An additional 1 liter of LB solution was added to the culture, which was then grown to OD$_{600}$ 1.0. IPTG was then added to a final concentration of 1 mM and was incubated for 60 min at 37° C. The culture was centrifuged for 10 min at 4000 g at 4° C. Every 5 g pellets were lysed by 50 ml GdnHCl (8M, 300 mM NaCl, 50 mM K$_2$HPO$_4$/KH$_2$PO$_4$, pH=8) for 12 hrs at room temperature. Supernatants of the lysates were collected at 12,000×g for 30 min before loading onto a His-Select Ni-NTA column. The column was washed with KPI (300 mM NaCl, 50 mM K$_2$HPO$_4$/KH$_2$PO$_4$, pH=8) buffer and 20 mM imidazole KPI buffer, then eluted with 300 mM imidazole KPI buffer.

Purification of mCherry-Spycatcher and GFP-Snoopcatcher

Cell seeds harboring plasmids that express mCherry-Spycatcher or GFP-snoopcatcher proteins were inoculated in 5 mL LB culture solution and cultured overnight at 37° C. The seed culture was then added into 1 liter LB for growth until OD$_{600}$ reaches 0.6. IPTG was then added into the culture with a final concentration of 0.5 mM. The cell culture continued for another 12 hrs at 16° C. Cell pellets were then collected through centrifugation and then lysed with lysozyme buffer (20 mg/mL) on ice for 30 min. During cell lysis, ultra-sonication was applied for 3 times at ~60% power (10 s on, 30 s off). The remaining purification procedures followed the same protocol as CsgA-fusion proteins.

3. Preparation for Ink

Proteins Ink

Solutions containing purified protein monomers were statically incubatedover night. The self-assembled nanofibers were dialysised (3 kDa, Yeasen) with ddH$_2$O for 72 hrs to remove salts and then freeze dried. Every 3 mg powders were then dissolved in 1 mL HFIP until complete dissolution. Before use, the solution was filtered with a 220 nm PTFE filter (Millipore). As HFIP is a toxic and voltaic solvent, all the procedures were performed in the fume hood.

Protein/Chitin Ink

Protein/chitin complex ink was prepared by dissolving protein (2 mg/ml) and chitin nanofibers (2 mg/mL) in HFIP. Chitin nanofiber ink was prepared following a previously published procedure. In brief, 0-chitin powder (Industrial Research Ltd-New Zealand) is dissolved in HFIP over one week with occasional stirring. Before use, the solution was filtered with a 220 nm PTFE filter (Millipore).

4. Patterns Fabrication Through Microtransfer Molding Process

PDMS Molds Preparation

PDMS molds were produced by casting mixed pre-polymer and curing agent at 10:1 on silicon mold (width and depth of spider pattern are at 1 μm) in a PS culture dish, then put in a oven for about 4 hours at 70° C. following vacuum degassing. After cured, cut PDMS into defined shape with razor blade.

Substrate Cleaning

Silicon and glass substrates were immersed in piranha (Saturated H$_2$SO$_4$ and 30% aqueous H$_2$O$_2$, 7:3 by volume) and heated over-night, then cleaned by ultrasonic in acetone in isopropanol solution for 30 mins respectively. For ITO and Au (thermal evaporated on silica) substrate, they are cleaned by ultrasonic in acetone in isopropanol solution for 30 mins respectively. For PS substrate, it is cleaned by ultrasonic in ethanol solution for 30 mins. Finally, all substrates are washed by ddH$_2$O and dried by high-pressured N$_2$ gas.

Patterning Process Through Microtransfer Molding

20 μL of the prepared protein ink (3 mg/mL) were dropped on a clean slide glass, and a pre-fabricated PDMS stamp were gently placed on top of the protein ink and incubated for 1 second to allow complete diffusion. The PDMS using a clean tweezers to objective substrate and incubate for 15-30 minutes.

Renaturing Process

After peeling off the PMDS, samples were placed above methanol solution bubbled by gentle N$_2$ gas for at least one week, then put in the methanol solution overnight.

Free-Standing Patterns Fabrication

PVA (5%) solution was dropped on glass substrate and formed a sacrificial layer. After pattern and renaturing process, sacrificial layer was washed by ddH$_2$O.

5. Stability Test

Stability of Protein Powder Samples

FTIR spectra were carried out to determine the stability of structures under different conditions by comparing the characteristic peaks of belta-sheet in samples before and after challenge.

For long-term stability test, protein nanofiber powders (after curing in methanol atomsphere) were placed in cabinet for 6 months (20° C., 60% relative humidity). For extreme temperature tests, powders were placed in an oven (90° C.) and refrigerator (−80° C.). For stability tests in aqueous bufferor organic solvents, samples were placed in 1 mL centrifuge tubes filled with liquid for 24 hrs. Before FTIR spectra characterization, samples were freeze-dried to remove liquid completely.

Stability of Patterned Samples

Stability of patterned structures, challenged under different extreme conditions, was based on the morphology and height changes of the structures based on AFM height images. For long-term stability test, patterns on silicon substrate were placed in cabinet for 6 months (20° C. 60% relative humidity). For extreme temperature tests, patterns were placed in an oven (90° C.) and refrigerator (−80° C.). For tests of aqueous buffers and organic solvents, patterns were placed in glass culture dish covered with liquid for 24 hrs. Before AFM height image characterization, patterns were washed by ddH$_2$O and dried by high-pressured N$_2$ gas.

6. Ni-NTA Capped QDs and Au NPs Assembly Process

PAM patterns on glass substrate (1 cm$^2$) were incubated with 200 μL Au NPs or QDs (0.1 mg/mL) solution for 30 mins, and washed with ddH$_2$O and dried with N$_2$ flow. Synthesis and ligand exchange of QDs and Au NPs followed a procedure in a previous publication.

7. Conjugation of Fluorescent Proteins with Freestanding Patterned Porous PAMs Sheet Patterned PAMs on glass substrate (1 cm$^2$) were covered with 200 μL fluorescent protein solution (1 mg/mL) for 30 mins. The samples were then washed with ddH$_2$O and dried with N$_2$ flow.

8. Biomimetic Mineralization of SiO$_2$ on Freestanding Patterned Porous PAMs Sheet 60 μL of TEOS (1 M) and HCl (1 mM) solution was added on PAMs sheets for biomimetic silicification, and incubated for 10 min at ambient condition. After reaction, porous PAMs sheets were washed with ddH$_2$O and left to dry overnight in the fume hood.

9. Cell Experiments

Cell Culture

Human embryonic kidney cells (HEK-293, ATCC) were cultured in DMEM (Gibco, NY, USA) supplemented with 10% (v/v) FBS (Gibco, NY, USA) and 1% (v/v) penicillin/streptomycin solution (Biowest, France), at 37° C., 5% Co$_2$.

Transfections

Cells were transfected with pSEAP2-Control (P$_{SV40}$-SEAP-pA; SEAP, human placental secreted alkaline phosphatase; Clontech) and pmCherry2-C1(P$_{CMV}$-mCherry-pA; Addgene). In brief, 5×10$^4$ cells seeded per well of a 24-well plate 18-20 h prior to transfection were incubated for 6 h with 50 μL of a 3:1 PE:DNA mixture (w/w) (polyethyleneimine, MW 40,000; Polysciences, Germany) containing 0.3 μg of total DNA in serum- and antibiotic-free DMEM.

MTT Assay

In brief, 5×10$^4$ HEK-293T cells were seeded per well in a 24-well plate and cultured for 72 h in the presence of various concentrations of OA; 40 μL of MTT (5 mg/ml in PBS) was then added to each well and incubated at 37° C. for 4 h, followed by addition of 600 μL DMSO to each well until the purple formazan crystals completely dissolved. The characteristic absorption was measured using a microplate reader (BioTek Instruments, Inc.) at 490 nm.

Reporter Gene Assays mCherry expression was visualized using anLEICA microscope (LEICA DMi8), equipped with anLEICA digital camera (LEICADFC9000 GT), a 20×objective, and Leica Application Suite software (LAS X). The expression of SEAP in cell culture supernatants was quantified using a pNpp-based light absorbance time course. Briefly, 80 μL heat-inactivated cell culture supernatant (65° C., 30 min) was added to 120 μL of substrate solution (100 μL of 2×SEAP assay buffer containing 20 mMhomoarginine, 1 mM MgCl$_2$, 21% diethanolamine, pH=9.8 and 20 μL substrate solution containing 120 mMpNpp, p-nitrophenylphosphate), and the light absorbance was recorded at 405 nm (37° C.) for 10 min using a microplate reader (BioTek Instruments, Inc.) using Gen5 software.

Gene Construction

| Type | Name | Length (aa) | Function |
| --- | --- | --- | --- |
| Short peptide | CsgA$_{RGD}$ | 3 | Cell adhesion |
| | CsgA$_{AG4}$ | 12 | Silver ions reduction |
| | CsgA$_{AG3}$ | 12 | Silver ions reduction |
| | CsgA$_{spytag}$ | 13 | Protein conjugation |
| | CsgA$_{snooptag}$ | 15 | Protein conjugation |
| | CsgA$_{BSP}$ | 15 | Antibacterial |
| | CsgA$_{VN}$ | 15 | Stem cell |
| | CsgA$_{R5}$ | 18 | Bio-mineralization |
| | CsgA$_{HNP2}$ | 18 | Antibacterial |
| Protein domain | CsgA$_{SMAP29}$ | 29 | Antibacterial |
| | CsgA$_{10\times RGD}$ | 30 | Cell adhesion |
| | $_{spytag}$CsgA$_{CBD}$ | 13 + 45 | Double functions |
| | $_{snooptag}$CsgA$_{CBD}$ | 15 + 45 | Double functions |
| | $_{R5}$CsgA$_{CBD}$ | 18 + 45 | Double functions |
| | CsgA$_{P74}$ | 63 | Platinum nano crystals synthesis |
| | CsgA$_{VF0530}$ | 80 | Double-strands DNA binding |
| | CsgA$_{LL37}$ | 90 | Antibacterial |
| | CsgA$_{SSB}$ | 178 | Single-strands DNA binding |
| Enzyme | $_{Xylanase}$CsgA | 212 | Degradation of xylan |
| | $_{amylase}$CsgA | 524 | Hydroxylation of starch |

The invention claimed is:

1. A material fabrication method comprising:
(a) fabricating a structure from a programmable amyloid material (PAM) ink comprising an amyloid monomer stabilized in a liquid solvent; and
(b) contacting the structure with a curing agent which triggers polymerization of the amyloid monomer and stabilization of the structure, wherein (i) the curing agent is an alcohol which triggers intrinsic amyloid assembly but maintains the morphology of the structure, or (ii) the contacting step comprises a two-step cure: first contacting with a first cure agent in vapor phase, and second contacting with a second cure agent in liquid phase.

2. The method of claim 1 wherein the amyloid monomer is CsgA, FUS, TDP or TasA.

3. The method of claim 2 wherein the fabricating step comprises micro-transfer molding.

4. The method of claim 2 wherein the amyloid monomer is functionalized with one or more functional groups selected from active enzymes, isopeptide tags, cell affinity tags, and antibacterial, cell proliferation or differentiation peptides.

5. The method of claim 2 wherein the structure comprises a 3D array.

6. The method of claim 2 wherein the structure comprises self-supporting patterned porous PAM sheets (PPPS).

7. The method of claim 2 wherein after the contacting step the structure remains structurally and functionally stable after challenge with harsh conditions comprising high temperature 90° C., low temperature −80° C., aqueous solutions of low pH 2 and high pH 12, and organic solvents hexane, acetone, chloroform, isopropanol, and dimethylformamide.

8. The method of claim 2 wherein the method further comprises selectively degrading the structure with an enzyme.

9. The method of claim 1 wherein the fabricating step comprises micro-transfer molding.

10. The method of claim 1 wherein the monomer is functionalized with one or more functional groups selected from active enzymes, isopeptide tags, cell affinity tags, and antibacterial, cell proliferation or differentiation peptides.

11. The method of claim 1 wherein the solvent is a polar solvent which serves as a hydrogen-bond-donor, and solubilizes the amyloid monomer through hydrogen bond disruption, and does not form bonds with the amyloid monomer, wherein the solvent can dissolve amyloid structure and disrupt β sheets structures.

12. The method of claim 1 wherein the curing agent is an alcohol which triggers intrinsic amyloid assembly but maintains the original morphology of created structures.

13. The method of claim 1 wherein the contacting step comprises a two-step cure: first contacting with a first cure agent in vapor phase, and second contacting with a second cure agent in liquid phase.

14. The method of claim 1 wherein the structure comprises a 3D array.

15. The method of claim 1 wherein the structure comprises self-supporting patterned porous PAM sheets (PPPS).

16. The method of claim 1 wherein after the contacting step the structure regains β-sheets after curing.

17. The method of claim 1 wherein after the contacting step the structure remains structurally and functionally stable after challenge with harsh conditions comprising high temperature 90° C., low temperature −80° C., aqueous solutions of low pH 2 and high pH 12, and organic solvents hexane, acetone, chloroform, isopropanol, and dimethylformamide.

18. The method of claim 1 wherein the method further comprises selectively degrading the structure with an enzyme.

19. The method of claim 1 wherein the amyloid monomer is CsgA.

20. The method of claim 1 wherein the curing agent is methanol.

21. The method of claim 1 wherein the solvent is a polar solvent selected from hexafluoroisopropanol (HFIP) and trifluoroacetic acid (TFA).

22. The method of claim 1 wherein:
(i) the amyloid monomer is CsgA;
(ii) the curing agent is methanol; and
(iii) the solvent is a polar solvent selected from hexafluoroisopropanol (HFIP) and trifluoroacetic acid (TFA).

\* \* \* \* \*